United States Patent [19]

Lebioda et al.

[11] Patent Number: 5,763,490
[45] Date of Patent: Jun. 9, 1998

[54] TREATING PROSTATE CANCER WITH TARTRATE IONS

[75] Inventors: Lukasz Lebioda; Clarissa G. Jakob, both of Columbia, S.C.

[73] Assignee: University of South Carolina, Columbia, S.C.

[21] Appl. No.: 758,213

[22] Filed: Nov. 27, 1996

Related U.S. Application Data

[63] Continuation-in-part of Ser. No. 650,659, May 20, 1996, abandoned, which is a continuation of Ser. No. 309,091, Sep. 20, 1994, abandoned.

[51] Int. Cl.$^6$ .................... A61K 31/19; A01N 37/00; C12N 9/22
[52] U.S. Cl. ............................. 514/574; 435/199
[58] Field of Search .................. 435/199; 424/94.6; 514/574

[56] References Cited

U.S. PATENT DOCUMENTS

| | | | |
|---|---|---|---|
| Re. 33,405 | 10/1990 | Chu et al. | 435/7.23 |
| 3,823,071 | 7/1974 | Roy et al. | 435/21 |
| 4,205,130 | 5/1980 | Vihko | 435/196 |
| 4,267,272 | 5/1981 | Josephson | 435/7.4 |
| 4,444,748 | 4/1984 | Noble | 514/270 |
| 4,468,465 | 8/1984 | Sato | 436/64 |
| 4,710,469 | 12/1987 | Liang et al. | 435/194 |
| 4,946,688 | 8/1990 | Fahim | 424/643 |
| 5,013,645 | 5/1991 | Kim | 435/7.92 |
| 5,015,466 | 5/1991 | Parran, Jr. et al. | 424/52 |
| 5,071,658 | 12/1991 | Fahim | 424/643 |
| 5,128,118 | 7/1992 | Carroll et al. | 424/1.85 |
| 5,234,698 | 8/1993 | Fahim | 424/643 |
| 5,250,734 | 10/1993 | Rossignol et al. | 564/355 |
| 5,300,294 | 4/1994 | Johnson | 424/423 |

OTHER PUBLICATIONS

Foti et al. (1977) "Comparison of Human Prostatic Acid Phosphatase by Measurement of Enzymatic Activity and by Radioimmunoassay", *Clin. Chem.*, 23(1), 95–99.

Mukhopadhyay et al. (1989) "Inhibition of Neutrohil and Natural Killer Cell Function by Human Seminal Fluid Acid Phosphatase", *Clin. Chim. Acta*, 182, 31–40.

Carter et al. (1990) "Clinical Evidence for and Implications of the Multistep Development of Prostate Cancer", *J. Urol.*, 143, 742–746.

Dixon (1992) "Computer–Aided Drug Design: Getting the Best Results", *Trends Biotechnol*, 19, 357–363.

Schneider et al. (1993) "Three–Dimensional Structure of Rat Acid Phosphatase", *Embo J.*, 12(7), 2609–2615.

*Primary Examiner*—Jon P. Weber
*Attorney, Agent, or Firm*—Michael A. Mann

[57] ABSTRACT

A method is disclosed for treating prostate cancer in males by administration of tartrate ions from a tartrate derivative. The tartrate ions in the bloodstream bind to and inhibit prostatic acid phosphatase.

5 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 386 amino acids
( B ) TYPE: Amino acid
( C ) STRANDEDNESS: Not Applicable
( D ) TOPOLOGY: Linear ( x i ) SEQUENCE DESCRIPTION: SEQ ID NO:1:

```
Met  Arg  Ala  Ala  Pro  Leu  Leu  Leu  Ala  Arg  Ala  Ala  Ser  Leu  Ser
  5                      10                      15

Leu  Gly  Phe  Leu  Phe  Leu  Leu  Phe  Phe  Trp  Leu  Asp  Arg  Ser  Val
 20                      25                      30

Leu  Ala  Lys  Glu  Leu  Lys  Phe  Val  Thr  Leu  Val  Phe  Arg  His  Gly
 35                      40                      45

Asp  Arg  Ser  Pro  Ile  Asp  Thr  Phe  Pro  Thr  Asp  Pro  Ile  Lys  Glu
 50                      55                      60

Ser  Ser  Trp  Pro  Gln  Gly  Phe  Gly  Gln  Leu  Thr  Gln  Leu  Gly  Met
 65                      70                      75

Glu  Gln  His  Tyr  Glu  Leu  Gly  Glu  Tyr  Ile  Arg  Lys  Arg  Tyr  Arg
 80                      85                      90

Lys  Phe  Leu  Asn  Glu  Ser  Tyr  Lys  His  Glu  Gln  Val  Tyr  Ile  Arg
 95                     100                     105

Ser  Thr  Asp  Val  Asp  Arg  Thr  Leu  Met  Ser  Ala  Met  Thr  Asn  Leu
110                     115                     120

Ala  Ala  Leu  Phe  Pro  Pro  Glu  Gly  Val  Ser  Ile  Trp  Asn  Pro  Ile
125                     130                     135

Leu  Leu  Trp  Gln  Pro  Ile  Pro  Val  His  Thr  Val  Pro  Leu  Ser  Glu
140                     145                     150

Asp  Gln  Leu  Leu  Tyr  Leu  Pro  Phe  Arg  Asn  Cys  Pro  Arg  Phe  Gln
155                     160                     165

Glu  Leu  Glu  Ser  Glu  Thr  Leu  Lys  Ser  Glu  Glu  Phe  Gln  Lys  Arg
170                     175                     180

Leu  His  Pro  Tyr  Lys  Asp  Phe  Ile  Ala  Thr  Leu  Gly  Lys  Leu  Ser
185                     190                     195

Gly  Leu  His  Gly  Gln  Asp  Leu  Phe  Gly  Ile  Trp  Ser  Lys  Val  Tyr
200                     205                     210

Asp  Pro  Leu  Tyr  Cys  Glu  Ser  Val  His  Asn  Phe  Thr  Leu  Pro  Ser
215                     220                     225

Trp  Ala  Thr  Glu  Asp  Thr  Met  Thr  Lys  Leu  Arg  Glu  Leu  Ser  Glu
```

-continued

|  |  |  |  |  | 230 |  |  |  | 235 |  |  |  | 240 |
|---|---|---|---|---|---|---|---|---|---|---|---|---|---|
| Leu | Ser | Leu | Leu | Ser | Leu | Tyr | Gly | Ile | His | Lys | Gln | Lys | Glu Lys |
| 245 |  |  |  |  | 250 |  |  |  | 255 |  |  |  |  |
| Ser | Arg | Leu | Gln | Gly | Gly | Val | Leu | Val | Asn | Glu | Ile | Leu | Asn His |
| 260 |  |  |  |  | 265 |  |  |  | 270 |  |  |  |  |
| Met | Lys | Arg | Ala | Thr | Gln | Ile | Pro | Ser | Tyr | Lys | Lys | Leu | Ile Met |
| 275 |  |  |  |  | 280 |  |  |  | 285 |  |  |  |  |
| Tyr | Ser | Ala | His | Asp | Thr | Thr | Val | Ser | Gly | Leu | Gln | Met | Ala Leu |
| 290 |  |  |  |  | 295 |  |  |  | 300 |  |  |  |  |
| Asp | Val | Tyr | Asn | Gly | Leu | Leu | Pro | Pro | Tyr | Ala | Ser | Cys | His Leu |
| 305 |  |  |  |  | 310 |  |  |  | 315 |  |  |  |  |
| Thr | Glu | Leu | Tyr | Phe | Glu | Lys | Gly | Glu | Tyr | Phe | Val | Glu | Met Tyr |
| 320 |  |  |  |  | 325 |  |  |  | 330 |  |  |  |  |
| Tyr | Arg | Asn | Glu | Thr | Gln | His | Glu | Pro | Tyr | Pro | Leu | Met | Leu Pro |
| 335 |  |  |  |  | 340 |  |  |  | 345 |  |  |  |  |
| Gly | Cys | Ser | Pro | Ser | Cys | Pro | Leu | Glu | Arg | Phe | Ala | Glu | Leu Val |
| 350 |  |  |  |  | 355 |  |  |  | 360 |  |  |  |  |
| Gly | Pro | Val | Ile | Pro | Gln | Asp | Trp | Ser | Thr | Glu | Cys | Met | Thr Thr |
| 365 |  |  |  |  | 370 |  |  |  | 375 |  |  |  |  |
| Asn | Ser | His | Gln | Gly | Thr | Glu | Asp | Ser | Thr | Asp |  |  |  |
| 380 |  |  |  |  | 385 |  |  |  |  |  |  |  |  |

TREATING PROSTATE CANCER WITH TARTRATE IONS

The present application is a continuation-in-part application of co-pending U.S. patent application Ser. No. 08/650,659 filed May 20, 1996, which is a continuation application of U.S. patent application Ser. No. 08/309,091 filed Sep. 20, 1994, now abandoned.

BACKGROUND OF THE INVENTION

1. Field of the Invention:

The present invention relates to a method for treating prostate cancer. In particular, the present invention relates to a method for treating prostate cancer by inhibiting the activity of human prostatic acid phosphatase (hPAP) thereby allowing the body's immune system to combat the prostate cancer.

2. Discussion of Background:

Prostate cancer is the second most common cancer among men. Annually, in the United States approximately 100,000 patients are diagnosed with prostate cancer. Approximately 3% of all men die as a consequence of this disease.

Currently, it is known to treat patients with prostate cancer by hormonal therapy to retard the growth of the cancer cells. One type of hormonal therapy involves the inhibition of the steroidal hormone androgen. Administration of anti-androgens to patients with prostrate carcinomas is known to decrease the growth of prostate carcinoma cells. Garnick, (1994) *Scientific American* 270, (4) 72–81.

Other forms of hormonal treatment of prostate cancer are disclosed in U.S. Pat. No. 5,300,294, issued to Johnson, and U.S. Pat. No. 5,234,698, issued to Fahim. Johnson discloses the use of steroid 5-alpha-reductase inhibitors to treat prostate cancer. The steroid 5-alpha-reductase inhibitors disclosed in Johnson have been shown to have a therapeutic effect on prostatic carcinoma in mammals.

Similarly, Fahim teaches a method of treatment for early prostatic carcinoma using zinc ions to inhibit the rate of prostatic growth. The treatment disclosed in Fahim controls the rate of prostatic growth by inhibiting androgen receptors or by interfering with the enzymatic conversion of testosterone to 5-alpha-dihydrotestosterone (DHT).

Unfortunately, almost all metastatic tumors become resistant to hormonal therapy at some point and then progress rapidly. The present invention is distinct in that it protects the body's natural defense mechanisms by inhibiting prostatic acid phosphatase so the body can fight the cancer naturally.

Protein phosphatases together with protein kinases play a crucial role in many aspects of cell function. Prostatic acid phosphatase, unlike most protein phosphatases, is not a membrane protein but is produced by the prostate gland and found at relatively high concentrations in seminal fluids (1 mg/mL). Because of its high concentration in seminal fluids, human prostatic acid phosphatase (hPAP), is often referred to as seminal fluid acid phosphatase. The prostatic acid phosphatase enzyme is active with a broad spectrum of substrates including phosphotyrosyl proteins, but its physiological role and the physiological substrate remain uncertain. It is, however, postulated that the physiological function of hPAP is to suppress the immune system in the vagina to protect the sperm cells. In a healthy body, the vast majority of hPAP enzyme is contained in the reproductive system. However, as prostate cancer develops, the cancer cells spread throughout the body secreting large quantities of the hPAP enzyme. Levels of the hPAP enzyme in blood serum have been used for monitoring the stage of prostate cancer for many years, thus the well known PAP test for prostate cancer.

The body's immune system fights the prostate cancer as the cancerous cells spread throughout the body. The immune system contains "natural killer" cells that act as a defense to diseases such as prostate cancer. However, the hPAP enzyme that acts to protect sperm from the female immune system in the vagina, now acts to suppress the body's own defense mechanism against cancer cells. The human prostatic acid phosphatase (hPAP), secreted in large quantities by prostate cancer cells, inhibits by 85% the ability of the body's natural killer cells to combat the cancerous cells. Glew, et al. (1989) *Clin. Chem. Acta* 182, 31–40. With the hPAP enzyme inactivating the natural killer cells, the cancer cells are able to escape attack by the body's immune system. Therefore, the presence of hPAP in blood serum and especially in the vicinity of the tumor cells effectively inhibits the body's anti-tumor immunological effector mechanisms. The presence of hPAP produces marked decreases in levels of cytotoxic effector cells infiltrating the tumor as well as effector cells which may control the metastatic spread of small tumor emboli. The correlation between the decrease in the activity of the natural killer cells and the presence of tumor cells in the blood stream has been reported. Therefore, the inhibition of human prostatic acid phosphatase would allow the body's own defense system to be restored and thus the spread of cancer reduced.

It is believed that inhibition of human prostatic acid phosphatase has not been employed as a method for treating prostate cancer. It is therefore an object of the present invention to treat prostate cancer by introducing a compound into a patient's body to inhibit prostatic acid phosphatase. It is furthermore an object of the present invention to prevent prostatic acid phosphatase from reducing the activity of the body's immune system, so that the immune system can serve as a natural defense against the cancer.

SUMMARY OF THE INVENTION

According to its major aspects and broadly stated, the present invention is a method for treating cancer, in particular, prostate cancer. The method comprises the step of binding a compound to prostatic acid phosphatase produced by prostatic cells to inhibit the activity of the prostatic acid phosphatase. The inhibitor compound is specifically adapted for prostatic acid phosphatase and binds to a binding region of the prostatic acid phosphatase enzyme thereby preventing the enzyme from reducing the activity of the natural killer cells.

An important advantage of the present invention is the restoration of the body's immune system, which is compromised by the prostatic acid phosphatase, so that the body's immune system is able to defend against the prostate cancer. This advantage arises because the compound bound to the binding region of the prostatic acid phosphatase prevents the bound hPAP from binding molecules associated with the immune system. Therefore, the hPAP inhibitory complex has no autoimmune-suppressive effect.

An important feature of the present invention is the use of the L-tartrate ion or a tartrate ion derivative as the prostatic acid phosphatase inhibitor. The inhibitor will readily bind to the binding region of PAP and thus prevent other ions and compounds from doing so.

Another feature of the present process is that the binding step further comprises the step of introducing the inhibitor compound into the blood stream, so that the inhibitor compound can bind to the prostatic acid phosphatase in the blood stream. The invention further comprises an inhibitor compound that is permeable to the prostatic cell membrane and is thus able to inhibit the prostatic acid phosphatase enzyme within the cell.

Furthermore, another feature of this invention is a L-tartrate derivative-prostatic acid phosphatase complex composition for treating prostate cancer. The L-tartrate derivative-prostatic acid phosphatase complex is formed in the body or in vivo (In vivo pertains to a biological reaction taking place in a living cell or organism). The composition comprises approximately one molecule of a (L)-tartrate derivative and approximately one subunit of human prostatic acid phosphatase, wherein the prostatic acid phosphatase has a binding region and the L-tartrate derivative is specifically adapted to the binding region of the hPAP. Because the native hPAP consists of two subunits with each subunit believed to contain one binding region, one molecule of L-tartrate is needed for each subunit.

In addition, another feature of the present invention is a composition for treating prostate cancer made according to the process comprising the steps of introducing a compound adapted to be specific for hPAP into a body, wherein the body includes hPAP produced by prostatic cells, binding the compound to the hPAP to form a complex composition between the compound and the human prostatic acid phosphatase.

Moreover, another feature of the present invention is that the formulation of an inhibitor is based on the crystallographic studies of the PAP enzyme and of complexes between the PAP enzyme and the inhibitor compounds.

Other features and advantages of the present invention will be apparent to those skilled in the art from a careful reading of the Detailed Description of a Preferred Embodiment presented below.

DETAILED DESCRIPTION OF A PREFERRED EMBODIMENT

Figure 1:
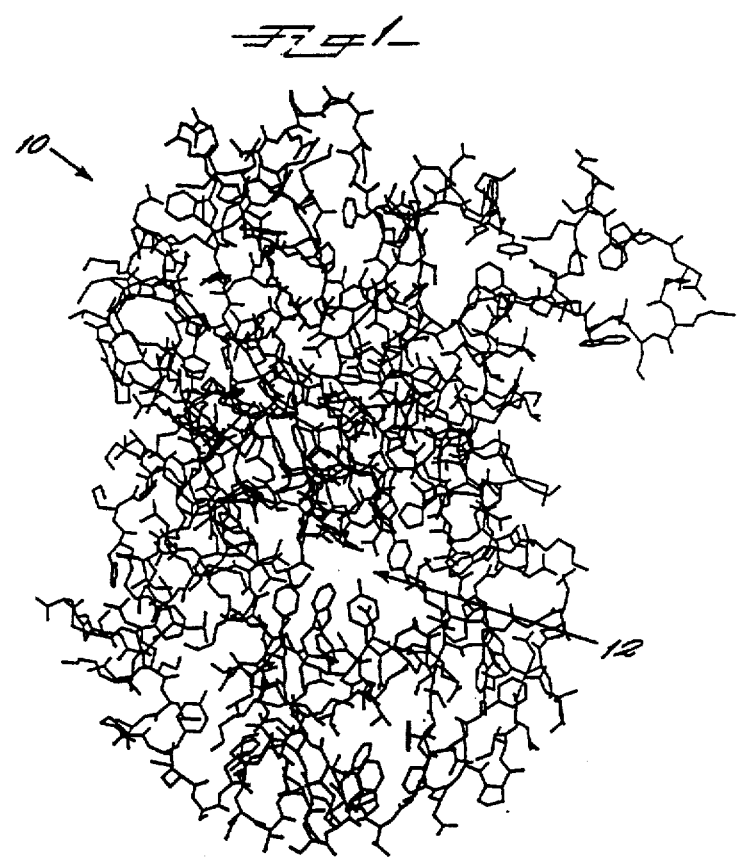
FIG. 1 is a representation of the molecular structure of one subunit of human prostatic acid phosphatase.

According to a preferred embodiment of the present invention, the development of highly specific inhibitors to treat prostate cancer is based on crystallographic studies of human prostatic acid phosphatase (hPAP). In addition, the development of specific inhibitors for human prostatic acid phosphatase is based on applications of molecular modeling to drug design.

Human prostatic acid phosphatase (hPAP) represents one of the most important secretory products of the prostate gland. The enzyme is a non-specific phosphomonoesterase hydrolyzing a wide range of alkyl, aryl and acyl orthophosphate monoesters, including phosphotyrosine according to the general reaction:

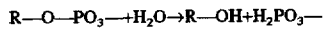

Human prostatic acid phosphatase (hPAP) has also been found to dephosphorylate macromolecules including oligonucleotides, polynucleotides and phosphotyrosyl-proteins. Of substrates investigated, alpha-naphtyl phosphate is most rapidly hydrolyzed by hPAP. p-Nitrophenyl phosphate (PNPP) is also hydrolyzed rapidly by hPAP. PNPP is traditionally the most commonly used substrate because it can be accurately and easily quantitated in a spectrometric assay. Phosphate groups can also be split from creatine phosphate which has an N-P bond. Compounds that are resistant to hPAP are pyrophosphate, phosphoanhydlides and S-substituted monoesters of phosphorothioic acid. Like most other non-specific phosphomonoesterases hPAP has the ability to catalyze the transfer of phosphoryl groups to hydroxyl compounds. There is a trend towards greater transfer with an increase in the number of carbon atoms in the acceptor alcohol.

Human prostatic acid phosphatase (hPAP) is categorized as an acid phosphatase since it has an optimum pH in the range 4 to 7. The catalytic mechanism has been intensely studied and it has been concluded that the enzyme can be classified as a histidine phosphatase. The crucial intermediate is a phosphoroamidate, namely phosphohistidine. The rate limiting step is the breakdown of this covalent phosphoenzyme intermediate by attack of water on the phosphoroamidate, with the formation of a non-covalent enzyme-inorganic phosphate complex.

The primary translation product that leads eventually to the mature prostatic acid phosphatase enzyme is a precursor polypeptide of 112 kDa. The precursor polypeptide is processed to mature polypeptides of 59, 55 and 49 kDa via an intermediate 91 kDa precursor. The precursor and mature polypeptides are glycosylated and contain a 32 amino acid leader sequence that directs the chain to the endoplasmic reticulum. The amino acid sequence of human prostatic acid phosphatase as reported by Van Etten et al., "Covalent Structure, Disulfide Bonding, and Identification of Reactive Surface and Active Site Residues of Human Prostatic Acid Phosphatase" *J. Biol. Chem.* 266, 2313-2319 (1991), is shown in Seq. ID No.:1 in the appended Sequence Listing.

In the amino acid sequence, the mature peptide begins with residue 33. The hPAP enzyme is secreted into the spermatic fluid where the mature, cleaved protein is found in very high concentrations, about 1 mg/mL. The enzyme isolated from the spermatic fluid is more homogenous than preparations obtained from prostatic tissues.

Acid phosphatases are widely distributed in both the animal and plant kingdoms. They have been divided into three broad classes. The first includes low molecular weight phosphatases 18-20 kDa per subunit as found in human liver, the second 45-60 kDa per subunit such as prostatic, lysosomal, and wheat germ enzymes. Only this class of enzymes is inhibited by tartrate. The third class includes metalloenzymes which typically utilize two iron ions per active site. The three classes are not homologous and the structures of the enzymes are different. There is, however, a 49% sequence identity between the lysosomal and prostatic enzyme which indicates common ancestry and similar structure and mechanism. Native hPAP is a glycoprotein of molecular weight approximately 100 kDa. The active hPAP is a dimer consisting of two subunits (or protomers) with very similar or identical molecular weights of 50 kDa. Each subunit of hPAP is believed to contain one active site which catalyzes the non-specific reactions mentioned above, hydrolysis of N- and O-linked phosphomonoesters and transphosphorylation.

Recent studies have shown that pre-incubation of natural killer cells with increasing amounts of hPAP bring a dose-dependent inhibition of the natural killer cells ability to kill the tumor target cells, (approximately 30 mU of hPAP inhibited killing by 85%, Glew et al., *Clin. Chem. Acta*, 182, 31–40). It has also been found that hPAP blocks superoxide production by neutrophils by 50%. Therefore, the secretion of large amounts of hPAP could effectively inhibit host anti-tumor immunological effector mechanisms, including both natural killer cells and acquired (neutrophils) immunity. In patients with prostate carcinoma, a decrease in natural killer cell activity level correlates with the presence of tumor cells in circulation (Tarle et al., *Urol. Res.*, 21, 17–21; Carter et al., *J. Urol.* 143, 742; Kastelan et al., *Prostate* 21, 111).

The physiological function of hPAP is postulated to be the suppression of the immune system in the vagina, to protect the sperm cells from the female's immune system. This suppression of the female's natural defense system renders the female more vulnerable to infections. Thus, inhibiting hPAP could also be useful as a method for preventing the spread of sexually transmitted diseases. In addition, the suppression of the protecting agent for the sperm could act as a means of birth control. The present composition can thus be used is these applications are well as treating prostate cancer.

The development of highly specific inhibitors for human prostatic acid phosphatase is based on crystallographic studies. In determining a composition and means of inhibition for the hPAP enzyme, it is necessary to determine the structure of hPAP using crystallographic studies. Until the present structure of hPAP was determined, as shown in FIG. 1, no reporting of successful crystallization of hPAP had been reported. From the crystal structure of the hPAP enzyme, the binding region can be located and inhibiting compounds can be designed using molecular modeling techniques.

The high quality crystals for X-ray structural determination are initially obtained in a two step process using the standard hanging drop vapor diffusion method. In the first step small crystals are obtained that may be used as "seed crystals" for the second step. Initial components of the droplet in the first step are 5.18 mg/ml purified hPAP which has been previously dialyzed against 10 mM citrate buffer pH=5.0, 0.01% $NaN_3$, and 50 mM ammonium sulfate (AS), 20% polyethylene glycol (PEG)-1450, 50 mM glycine buffer pH=10.0, and 50 mM KCl. The well solution contained 40% PEG-1450, 0.1M glycine buffer pH=10.0, and 0.1 M KCl. Small single crystals are produced overnight.

The next set of vapor diffusion experiments are hanging drop vapor diffusion experiments combined with the macro-seeding technique. The droplet contained 4.61 mg/ml purified hPAP as described above, 15% PEG-1450, 50 mM glycine buffer pH=10.0, and 50 mM KCl. The well solution contained 30% PEG-1450, 0.1M glycine pH=10.0, and 0.1 M KCl. The experiments were allowed to equilibrate for approximately 4 days. After that time, a small crystal grown by the previous method is added to the drop. Some of the crystals dissolve, and later yield large crystals of hPAP. Still others simply grow over the period of several weeks to several months to produce suitable crystals.

Additional experiments were conducted to determine the optimum conditions for the crystallization of hPAP. Hanging drop vapor diffusion experiments were conducted where the initial droplet contained 3.45 mg/ml purified hPAP, 15% PEG-1450, 50 mM glycine buffer pH=10.0, and 50 mM KCl, and the well solution contained 30% PEG-1450, 0.1M glycine pH=10.0, and 0.1M KCl. Large, high quality crystals of hPAP are produced without the need for macro-seeding after approximately four months.

The important components for producing hPAP crystals under these conditions rest on two important components, PEG-1450 and a pH of approximately 10. It is believed that the final pH of the droplet after equilibration is crucial, however, the final pH because of the small volume of the drop and the high concentration of PEG-1450 is difficult to determine precisely. However, the pH is lower than 10 since the initial protein solution contains 10 mM citrate buffer. Therefore, any buffer that produces the same final pH could yield suitable crystals of hPAP. Additionally the mode of vapor diffusion would probably not be critical in producing suitable crystals of hPAP. Other vapor diffusion set-ups which could be used include, but are not limited to: sitting drop, sandwich drop, and gel diffusion, using Linbro plates/tissue culture plates, sandwich boxes, capillaries, and Flow Laboratory's vapor diffusion plates for varying sitting and standing drop conditions.

The average crystal grown by successful macro-seeding measures 0.5×0.5×0.3 mm and diffracts X-rays to 3.0 Angstroms resolution using a 0.5 mm collimated Cu alpha radiation and an R-AXIS II imaging plate system. The crystals belong to the orthorhombic space group $P2_12_12_1$ and have unit cell dimensions a=126.3 Angstroms, b=207.9 Angstroms, and c=73.0 Angstroms. There are two dimers per asymmetric portion of the unit cell which give a V(m) =2.40 $Angstrom^3$/Da. Data for these crystals of hPAP were measured to 3.1 Angstrom resolution using an R-AXIS II imaging plate system.

The crystal structure of hPAP at 3.1 Angstroms resolution has been determined using the molecular replacement method with the structure of the rat enzyme as the model (Schneider, et al. (1993) *EMBO J.* 12, 2609–2615). The structure has been refined, without carbohydrate moieties and solvent, to a R=21 %. FIG. 1 is a representation of the structure for one subunit of the hPAP enzyme. As seen in FIG. 1, one subunit of the hPAP enzyme 10, includes a binding region 12, which contains an active site and at least one binding site. Amino acids in the binding region are strongly conserved. There are two binding regions per hPAP dimer, one binding region for each protomer.

FIG. 1 shows the atomic resolution structure of the polypeptide chain comprising the hPAP molecule but does not include the carbohydrate moieties. It is known that some heterogeneity of hPAP exists primarily because of differences in sialation. Some, but probably not all, structures for the carbohydrate moieties have been determined using Nuclear Magnetic Resonance Spectroscopy as reported by Risley et al., "Structures of the Carbohydrate Moieties of Human Prostatic Acid Phosphatase Elucidated by $^1H$ Nuclear Magnetic Resonance Spectroscopy" *Arch. Biocem. Biophys.* 258, 404–412 (1987), the disclosure of which is hereby incorporated by reference.

Compounds adapted to interact with the structure of hPAP bind to the hPAP enzyme resulting in the inhibition of the hPAP enzyme's ability to reduce the activity of the natural killer cells. Not wishing to be bound by theory, it is believed that the inhibitor compositions bind to the binding region (donut shaped cavity) of the hPAP enzyme, thus inhibiting the hPAP enzyme from attaching to other compositions such as the natural killer cells. The crystal structure of the PAP enzyme allows for not only the determination of the binding region, but also the structure of the binding region so that the compound may be selected and adapted specifically to the binding region. This tailoring of the inhibitor compound to the binding region allows for better binding and thus better inhibition. A compound that has a strong preference for hPAP, that is selective for it, is preferred. Furthermore, the compound should bind to enough of the binding region of the hPAP to prevent significant activity of the thus-bound hPAP.

Figure 2:
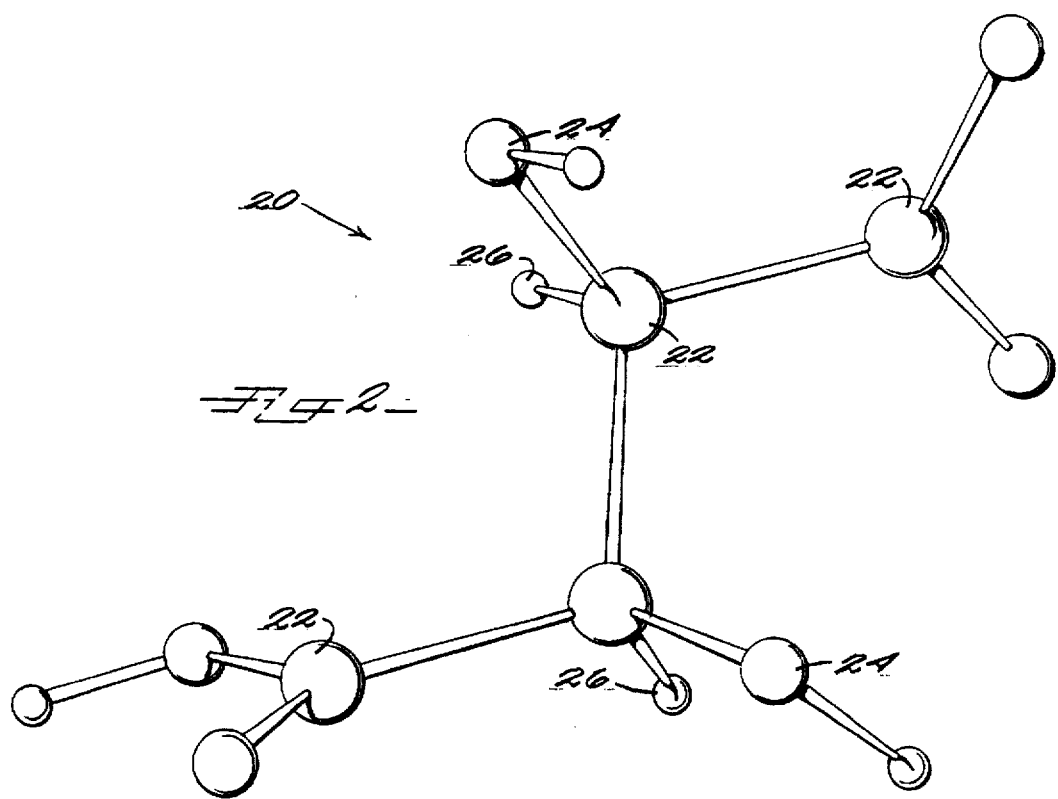
FIG. 2 is a representation of the molecular structure of the L-(+)-tartrate ion.

Examples of compositions compatible for binding with hPAP are tartrate ions and tartrate ion derivatives. L-tartrate is well soluble, specific for the PAP enzyme, and does not appreciably inhibit other phosphatases, Foti, et al., "Clinical Chemistry" 23 (1):9599 (1977). FIG. 2 is a drawing of the L-(+)-hydrogen tartrate ion 20, represented by the molecular formula ($C_4H_5O_6$). The carbon atoms are represented by the largest ellipsoids 22, the oxygen atoms represented by the medium-sized ellipsoids 24, and the hydrogen atoms are represented by the smallest ellipsoids 26. Because of its specific inhibitory properties, L-tartrate is commonly employed in PAP enzyme assays. Furthermore, the tartrate ion has the advantage of being non-toxic, often used as an additive in many food products to add tartness to the taste. L-tartrate derivatives that will bind more strongly to the binding region are preferred.

L-tartrate derivatives are prepared using the carboxylic functional group and the hydroxyl functional group present in tartaric acid. Both of these functional groups are easily derivatized forming an ester linkage. For example, the carboxylic group present in the tartaric acid can be reacted with alcohols or in particular aromatic alcohols like phenol to form benzoyl or naphthol to form naphthoyl derivatives. In addition, the hydroxyl group can be reacted with acids like benzoic acid or 1-naphthyl acetic acid to form an ester linkage. Not wishing to be bound by theory, it appears that binding is improved because the derivatives that contain an aromatic functional group can be bound in a hydrophobic pocket located in the binding region of hPAP. It is proposed that this binding between tartrate derivatives containing an aromatic functional group and the hydrophobic pocket of the binding region is a result of the interaction between the aromatic functionality and the residues present in the active site region, such as tryptophan (Trp) 174, tyrosine (Tyr) 178, Tyr 182, and Tyr 278. Basis for this proposal is that these amino acid residues are believed to bind to known substrates that have aromatic moieties, such as alpha-naphthyl-phosphate, phosphotyrosine and para-nitrophenylphosphate. Examples of hPAP inhibiting compounds include: tartrate ion, oxalic ion, methyl tartrate, ethyl tartrate, propyl tartrate, butyl tartrate, phenyl tartrate, toluyl tartrate, naphthyl tartrate, benzoyl tartrate, naphthoyl tartrate, acetoxy tartrate, 1-naphtoxy acetic acid, 1-naphtyl acetate and alpha-hydroxy 1-naphtyl acetate and combinations thereof.

Other compositions that may be useful as inhibitors are inorganic oxoanions like vanadate, molybdate and tungstate. In addition, heteropolyanions, which inhibit hPAP may also be used. Examples of these are: heteropolymolybdates, heteropolytungstates, heteropolyoxometalates and heteropolyperiodates. Useful heteropolyoxometalate complexes include: $[C(NH_2)_3]2[(CH_3)_2AsMo_4O_{15}H]$, $(Bu_4N)_2(CH_3)_2AsMo_4O_{15}H$, $(Bu_4N)_2(C_6H_5)_2AsMo_4O_{15}H$, $(Bu_4N)_2Mo_8O_{28}$, $(NH_4)_6Mo_7O_{24}\cdot 4H_2O$, $(NH_4)_3FeMo_6O_{24}H_6\cdot 6H_2O$, $(NH_4)_4GeMo_{12}O_{24}H_6\cdot xH_2O$, $Na_3PMo_{12}O_{40}\cdot xH_2O$, $(NH_4)_8ThMo_{12}O_{42}\cdot 7H_2O$, $(NH_4)_4(CH_3As)_4Mo_{12}O_{46}\cdot xH_2O$, $(NH_4)_6As_2Mo18O_{62}\cdot xH_2O$.

Furthermore, so-called "suicide" inhibitors which are excellent irreversible inhibitors may also be used, for example, 4-(fluoromethyl)phenyl phosphate. Both the oxoanion and "suicide" inhibitors, however are not specific for hPAP, and thus they may also inhibit other protein phosphatases.

Combinations and mixtures of the above PAP inhibitor compounds can also be used to treat prostate cancer by inhibiting the PAP enzyme.

Compounds employed as inhibitors should not be limited to the above mentioned compounds, but to compounds which effectively inhibit the PAP enzyme. More specifically, the compounds that are structurally specific to the binding region of the hPAP enzyme as defined by the crystal structure of the hPAP enzyme.

Persons skilled in the art can readily determine if a compound is a hPAP inhibitor by known methods. All such compounds are included within the scope of this invention.

The crystals of inhibitory complexes are obtained by soaking native crystals in artificial mother liquors containing inhibitors or by growing the crystals under suitable crystallization conditions in the presence of inhibitors. Tartaric acid and its salts are very well soluble and their derivatives have high solubility's in aqueous solutions. Tartrate ion binding by rat-PAP does not induce conformational changes and the tartrate ion does not cause crystal cracking in soaking experiments with hPAP crystals. If problems are encountered with crystal soaking in mother liquors with other inhibitors, the gradient diffusion method should be used, Lebioda (1992) *J. Appl. Crystallogr.* 25, 323–324. The inhibitors are located in difference Fourier maps and the structures of the inhibitory complexes refined by crystallographic restraint least-squares.

In the preferred embodiment of the invention, a PAP inhibitor is introduced into a body with prostate cancer. A PAP inhibitor is introduced into the body by means of injection, infusion over an extended period, orally in capsule, tablet form or by any other viable form, or may be applied directly in the form of a lotion, cream or similar form. Injection may be made directly into the blood stream or into the site of the cancer, so long as the inhibitor is available to the prostatic acid phosphatase desired to be inhibited.

Experiments on the activity of the human natural killer cells of the immune system are carried out using the target cell line K-562 and the natural killer cell activity of murine splenic cells is assayed using the YAC line. Procedures for measuring the natural killer cell activity are standard techniques, Gangemi, J. D. (1980) *J. Reticuloendothel. Soc* 27, 525–533. $^{51}$Cr-labeled target cells will be mixed with effector cells (non-adherent peripheral blood mononuclear cells) at various effector: target (100:1, 50:1 and 25:1) cell ratios. The cells are incubated for 4 hours and the amount of $^{51}$Cr released is measured. From the amount of radioactivity in the supernatant the percent cytotoxicity and number of lytic units is calculated. A lytic unit is defined as the number of effector cells that cause 33% cytotoxicity.

The natural killer cells inhibitory effect of PAP is quantitated by adding a known number of enzyme units to the cytotoxicity assay system and is expressed as the number of enzyme units required to inhibit one natural killer cell lytic unit. The natural killer cell restoratory effect of the PAP inhibitor compounds is determined by their addition to a natural killer cell target mixture containing PAP and expressed as the amount of compound causing 50% restoration.

Human monocytes or murine macrophages are activated in vitro by exposure to homologous interferon-gama for 16 hours in microtiter tissue culture plates and subsequently cultured with target cells (a human prostatic cancer cell line for human monoctyes or a mouse mammary adenocarcenoma line for murine macrophages). Alternatively, activated murine macrophages are obtained from mice treated with propionibacterium, then adhered to tissue culture microtiter plates and cocultured with tumor target cells. After 48 hours of co-culture, the cells are exposed to $^3$H thymidine for 61 hours and harvested for the measurement of thymidine incorporation. The degree of thymidine incorporation in target cells cultured with activated monocytes/macrophages verses their control cohorts reflect cytotoxic activity of macrophages. Addition of hPAP in this test allows the study of its inhibitory effect on macrophage anti-tumor activity and the addition of synthetic hPAP inhibitors allow for the measurements of the restoratory property of these compounds. The results are expressed as units of hPAP required to cause 50% inhibition of cytotoxicity and the amount inhibitor to affect a 50% restoration.

Clinical studies show that cancer patients, both male and female, diagnosed with forms of cancer other than prostate cancer, can have a significant amount of cancerous cells which express PAP. Consequently, it will be recognized by those with ordinary skill in the art that the administration of the L-tartrate ion or a tartrate ion derivative as a specific prostatic acid phosphatase inhibitor may be used as a method for treating other forms of cancer, besides prostate cancer, without departing from the spirit and scope of the present invention.

It will be apparent to those skilled in the art that many changes and substitutions can be made to the preferred embodiment herein described without departing from the spirit and scope of the present invention as defined by the appended claims.

What is claimed is:

1. A method for treating prostate cancer in the body of a male individual in need thereof, said body producing prostatic acid phosphatase, said method comprising the step of administering tartrate ions from a tartrate derivative to the male individual, said tartrate ions binding to said prostatic acid phosphatase in vivo to inhibit activity of said prostatic acid phosphatase.

2. The method as recited in claim 1, wherein said tartrate derivative is selected from the group consisting of tartrate esters, tartrate amides, tartaric acid, and tartrate salts.

3. The method as recited in claim 1, wherein said step of administering said tartrate derivative further comprises the step of introducing said tartrate derivative into the blood stream of said body of the male individual so that said tartrate ions can bind to said prostatic acid phosphatase in said blood stream of said body of the male individual.

4. The method as recited in claim 1, wherein said step of administering said tartrate derivative further comprises the step of injecting said tartrate derivative into the blood stream of said body of the male individual so that said tartrate ions can bind to said prostatic acid phosphatase in said blood stream of said body of the male individual.

5. The method as recited in claim 1, wherein said step of administering said tartrate derivative further comprises the step of ingesting said tartrate derivative so that said tartrate ions can be assimilated into said body of the male individual to bind with said prostatic acid phosphatase.

* * * * *